United States Patent [19]

Miller

[11] Patent Number: 4,996,340

[45] Date of Patent: Feb. 26, 1991

[54] INTRAMOLECULAR MIGRATION REACTIONS

[75] Inventor: Joseph A. Miller, Santa Rosa, Calif.

[73] Assignee: Ethyl Corporation, Richmond, Va.

[21] Appl. No.: 433,323

[22] Filed: Nov. 8, 1989

[51] Int. Cl.$^5$ ............................ C07F 5/06; C07C 2/76
[52] U.S. Cl. .................................. 556/190; 556/170; 556/183; 556/187; 585/601
[58] Field of Search ............... 556/190, 170, 186, 187, 556/189; 585/601, 600

[56] References Cited

U.S. PATENT DOCUMENTS 3,686,250 8/1972 Lanier .................................. 556/190
3,829,520 8/1974 Ferrell ............................ 556/190 X
4,133,815 1/1979 Watson et al. ................... 565/190 X
4,251,453 2/1981 Garrison .......................... 556/190 X Primary Examiner—Arthur C. Prescott
Attorney, Agent, or Firm—Richard J. Hammond

[57] ABSTRACT

A novel migratory insertion reaction is disclosed utilizing organoaluminum compounds. An intramolecular transfer of a carbon group from the aluminum complex E-1-halo-1-alkenyl)trialkylalanate occurs to produce an E-alkenyl(alkoxy)dialkylalanate or an E-dialkylalkenylalane or an (E,E)-3-alkyl-2-dialkylalumino-1,3-diene depending on process conditions. Novel organic aluminates are also disclosed.

31 Claims, No Drawings

INTRAMOLECULAR MIGRATION REACTIONS

FIELD

This invention relates to unprecedented intramolecular reactions in which a carbon group from aluminum migrates to an adjacent vinylic center in a stereospecific manner. Such reactions enable the synthesis of stereodefined olefins.

BACKGROUND

Many migratory insertion reactions have been reported in organoboron chemistry. They represent the most common method for synthesizing carbon-carbon bonds using boron. See Brown, H. C., *Organic Synthesis via Boranes:* Wiley-Interscience: New York 1975 and Negishi, E., *Organometallics in Organic Synthesis,* Vol. 1, Wiley-Interscience, New York, 1980, Chapter 5. However, analogous 1,2-migration reactions with the corresponding organoaluminums are not common. See Mole, J.; Jeffery, E. A., *Organoaluminum Compounds;* Elsevier: Amsterdam, 1972; Negishi, E., *Organometallics in Organic Synthesis,* Vol. 1, Wiley-Interscience, New York, 1980, Chapter 5; and Zweifel, G.; Miller, J. A., *Org. React.,* 1984, 32, 375–517. Some examples of organoaluminum reactions reported, in which migratory insertions appear to have occurred, include formation of homologous alanes by reaction of organoalanes with diazomethane (see Hoberg, H., *Ann. Chem.,* 1962, 656, 1; 1966, 695, 1; *Angew. Chem. Int. Ed. Engl.,* 1966, 5, 513) and the formation of a mixture of propargylic and allenic alanes from the reaction of lithium chloropropargylide with tri-n-hexylaluminum (see Zweifel, G., *Aspects of Mechanism and Organometallic Chemistry;* Brewster, J. H., Ed.; Plenum Press: New York, 1978; pp 229–249. Recently, Negishi and Akiyoshi (*J. Am. Chem. Soc.,* 1988, 110, 646), have reported that a variety of main group organometallics (including organoaluminums) in addition to boranes readily participate in 1,2-migration reactions.

THE INVENTION

In accordance with this invention, a new migratory insertion reaction of organoaluminum compounds is provided. In this reaction, a transfer of a carbon group from aluminum to the adjacent vinylic center occurs in alkali metal (1-halo-1-alkenyl) trialkylalanates. Moreover, this transfer occurs in a stereo-specific manner such that an alkali metal (E-1-halo-1-alkenyl)trialkylalanate is transformed mainly to (a) an alkali metal (E)-alkenyl(alkoxy)dialkylalanate, or (b) (E)-dialkylalkenylalane, and/or (c) (E,E)-3-alkyl-2-dialkyl-alumino-1,3-diene depending on how the process is conducted. Thus, in part, this invention represents for the first time an aluminum counterpart to the well known 1,2-migration reaction observed for the corresponding 1-halo-1-alkenylborates in the Zweifel trans-olefin synthesis (see Zweifel, G., Arzoumanian, H., *J. Am. Chem. Soc..* 1967, 89, 5086; Kobrich, G., Merkle, H., *Chem. Ber.,* 1967, 100, 3371; Zweifel, G, Fisher, R. P., Snow, J. T., Whitney, C. C., *J. Am. Chem. Soc.,* 1971, 93, 6309; Negishi, E., Katz, J. J., Brown, H. C., *Synthesis,* 1972, 555; Corey, E. J., Ravindranathan, T., *J. Am. Chem. Soc.,* 1972, 94, 4013; Negishi, E., Yoshida, T., *J. Chem. Soc., Chem. Commun.,* 1973, 606.

One embodiment of this invention involves a process for production of alkali metal alkenyl(alkoxy)dialkylalanate (2) in which the alkenyl group is predominantly (E) in structure, which comprises reacting an alkali metal alkoxide with an alkali metal (E-1-halo-1-alkenyl)trialkylalanate (1) in a non-protonic polar solvent, such that an alkyl group attached to the aluminum atom undergoes 1,2-migration to the carbon atom of the alkenyl group which is attached to the aluminum atom. This process is illustrated more generally by the following equation:

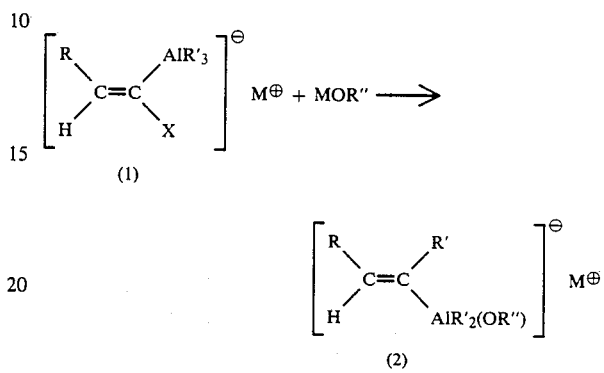

where R, R' and R" are the same or different and each is a $C_1$ to $C_{22}$ linear or branched hydrocarbon group (alkyl, alkenyl, alkynyl, cycloalkyl, aryl, aralkyl, etc.), preferably a primary hydrocarbyl group [primary alkyl group, primary alkenyl group, primary alkynyl group, primary cycloalkylalkyl group (cyclopropylcarbyl, etc.) primary aralkyl group (benzyl, 2-phenethyl, etc ), and the like.] Particularly preferred: are when R, R' and R" are $C_1$ to $C_{22}$ linear or branched primary alkyl group, most preferably $C_1$ to $C_{18}$ linear or branched primary alkyl group; X is a halogen atom, preferably a chlorine or bromine atom; and M is an alkali metal atom, preferably a sodium, potassium or lithium atom, most preferably a sodium atom. The hydrocarbon groups R, R' and R" may contain inert substituents such as ether linkages, thioether linkages, silane linkages, siloxy groups, sulfonyl groups, nitro groups, primary or secondary amino groups, and the like. In this connection, the term "inert" is used in the sense that the presence of such substituent(s) in the compounds being utilized in the process of this invention does not prevent the reaction from occurring nor prevent the formation of the product(s) anticipated to be produced thereby. Since both (a) unsubstituted hydrocarbyl groups (i.e., groups consisting of carbon and hydrogen only) and (b) hydrocarbyl groups substituted by one or more inert substituents, are themselves inert in the foregoing sense, the groups designated herein as R, R' and R" are in reality inert carbon-bonded organic groups.

The foregoing migratory insertion process is conducted at temperatures within the range of about 20° to about 80° C., and preferably in the range of about 40° to about 60° C.

In another embodiment of the present invention a 1,2-migration reaction is caused to take place in the absence of an alkali metal alkoxide by forming the alkali metal (trans-1-halo-1-alkenyl)trialkylalanate at a low temperature (e.g., below 10° C., preferably ~0° C.) and then warming the cold alkali metal (E-1-halo-alkenyl)-trialkylalanate in a non-protonic (i.e., aprotic) polar solvent to a temperature at which the 1,2-migration of the alkyl group occurs, e.g., about 25° C. or above, and preferably in the range of about 10° to about 40° C. In this case the product formed is an dialkylalkenylalane.

This embodiment thus provides a process for production of an dialkylalkenylalane (3) in which the alkenyl group is predominantly (E) in structure, which comprises warming a cold solution of an alkali metal (E-1-halo-1-alkenyl)trialkylalanate in a non-protonic polar solvent, such that an alkyl group attached to the aluminum atom undergoes 1,2-migration to the carbon atom of the alkenyl group which is attached to the aluminum atom. This reaction may be depicted generally as follows:

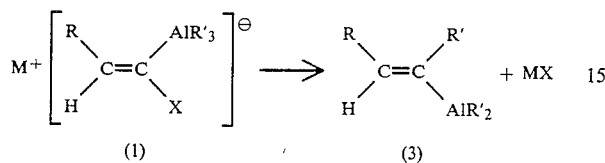

where R, R', X, and M are as defined above.

Another reaction of this invention occurs concurrently with the synthesis and subsequent heating of (1) as described above. In such reaction an 3-alkyl-2-dialkylalumino-1,3-diene (5) is formed. Thus in this embodiment there is provided a process for production of an alkali metal E,E-3-alkyl-2-dialkylalumino-1,3-diene (5), which comprises warming a cold solution of an alkali metal (E-1-halo-1-alkenyl)trialkylalanate (1) in a non-protonic polar solvent, such that an intermediate -1-alkyl-1-alkenyl(dialkyl)alane (3) is formed by elimination of an alkali metal halide from (2). Intermediate (3) redistributes with the alkali metal (E-1-halo-1-alkenyl)-trialkylalanate (1) to form an alkali metal E-1-alkyl-1-alkenyl(E-1-halo-1-alkenyl)dialkylanate (4). The cis-1-alkyl-1-alkenyl group then undergoes 1,2-migration to the carbon atom of the trans-1-halo-1-alkenyl group attached to the aluminum atom forming (5). This process may be depicted generally as follows:

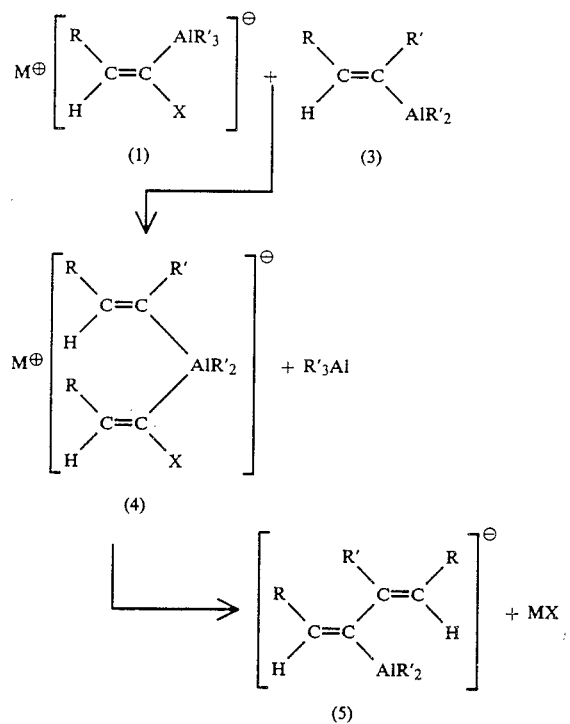

where R, R', X, and M are as defined above.

In this embodiment, initially the solution of alkali metal (1-halo-1-alkenyl)trihydrocarbylalanate (1) is kept at a low temperature (e.g., below ~0° C., preferably ~0° C.) and then warmed to a temperature at which the above depicted transformations, including the 1,2-migration of an alkyl group occur. Thus the temperature of the solution is raised to about 20° C. or above, and preferably in the range of about 15° to about 60° C.

Protonation of compounds (2) and (3) forms an internal olefin, cis-RCH=CHR', whereas protonation of compound (5) forms an (E—Z) conjugated alkadiene,

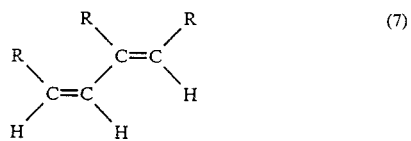

where R and R' are as defined above. The stereodefined olefins and dienes can be used in syntheses of a variety of derivatives.

Reaction of compound (2) or (3) with any of a wide variety of organic or inorganic electrophiles yields stereodefined trisubstituted alkenes. For example, reaction of compound (2) with iodine produces a trisubstituted alkene, E—RCH=CR'I. Other useful reactions of compound (2) include the following:

(a) Reaction of compound (2) with carbon dioxide enables production of unsaturated acids, E—RHC=CR'COOH.

(b) Reaction of compound (2) with formaldehyde enables production of unsaturated primary alcohols, E—RHC=CR'CH$_2$OH.

(c) Reaction of compound (2) with C$_2$ and higher aliphatic aldehydes, R'''CHO, enables production of unsaturated secondary alcohols, RHC=CR'CHR''OH, where R''' can be a variety of organic groupings.

(d) Reaction of compound (2) with organic or inorganic halosilanes (i.e., Q$_3$Si—X where the Q groups may be the same or different and are hydrogen atoms, halogen atoms, organic groups, etc.) enables production of substituted cis-vinyl silanes, RHC=CR'SiQ$_3$.

These and other useful synthesis reactions in which the foregoing alanates may be utilized will now be readily apparent to those skilled in the art.

To form the alkali metal (E-1-halo-1-alkenyl)trihydrocarbylalanates (compound (1)) used as the starting materials in each of the above embodiments, a regio- and stereospecific hydroalumination procedure is utilized. A preferred method involves reacting a 1-haloalkyne with an alkali metal aluminum trihydrocarbyl hydride at a temperature below about 10° C. in a non-protonic polar solvent. For further details, see Zweifel, G., Lewis, W., On, H. P., *J. Am. Chem. Soc.*, 1979, 101, 5101. It is convenient to conduct the processes of this invention in the same solvent medium used in forming compound (1).

The 1-haloalkynes in turn may be formed by known procedures such as the process described by Murray, R. E. *Synth. Commun.* 1980, 10, 345. Verboom, W.; Westmijze, H.; Denoten, L. J.; Vermeer, P.; Bos, H. J. T. *Synthesis* 1979, 296.

To form the alkali metal aluminum trihydrocarbyl hydrides a number of different procedures can be used.

For example a trihydrocarbyl aluminum compound may be reacted with an equimolar quantity of an alkali metal hydride in a non-protonic polar solvent. Alternatively an olefinic compound may be reacted with an alkali metal tetrahydride in a mol ratio of 3:1. Still another route involves reacting a hydrocarbyl alkali metal compound (e.g., RLi) with a dihydrocarbyl aluminum hydride in a 1:1 mol ratio. For further details, see Mole and Jeffery, op. cit.

The non-protonic dipolar solvents used in the practice of this invention should remain in the liquid state under the reaction conditions being employed. Illustrative of such solvents are dialkyl ethers such as diethyl ether, dipropyl ether, diisopropyl ether, dibutyl ether, methyl butyl ether; alkyl aryl ethers such as methyl phenyl ether (anisole); dialkyl ethers of ethylene glycol such as 1,2-dimethoxyethane, 1,2-diethoxyethane, 1,2-dibutoxyethane; dialkyl ethers of diethylene glycol such as diethylene glycol dimethyl ether (diglyme), diethylene glycol diethyl ether; cyclic ethers such as tetrahydrofuran, 2-methyltetrahydrofuran, 1,4-dioxane; N,N-dialkylamides such as N,N-dimethylformamide, N,N-dimethylacetamide; N-methyl-2-pyrrolidone; sulfolane; dimethylsulfoxide; and the like.

As noted above, a feature of the process of this invention is that it enables the synthesis of a variety of compounds in a regioselective and stereospecific manner.

Having described the basic concepts of this invention and the practice thereof, reference is now made to the following detailed explanation of specific reactions conducted in the laboratory and experimental details set forth in the form of examples, all of which information is presented for the purposes of illustration and not limitation. The term "Hex" is intended to mean n-$C_6H_{13}$ and "Bu" is n-$C_4H_9$.

EXAMPLE 1

(A) Preparation of cis-2-nonene via migratory insertion

Addition of 1-chloro-1-octyne to 1.5 equivalents of sodium trimethylaluminum hydride in diglyme at 0° C. with stirring for one hour resulted in the regio- and stereoselective formation of the E-alpha-chloroalkenylalanate, [HexHC=C(Cl)AlMe₃]⁻Na⁺, in 89% yield as evidenced from ¹H-NMR (the vinylic proton was present as a triplet, J=8 Hz, at 5.88 ppm) and gas chromatography (GC) analysis of the trans-1-chloro-1-octene obtained upon protonolysis. None of the corresponding cis-1-chloro-1-octene was observed by a gas chromatography comparison with an authentic sample. In addition, 11% of 1-octyne was found by gas chromatography. Allowing the reaction mixture to warm to room temperature and stirring for two hours produced by gas chromatography analysis cis-2-nonene (17%) with no trans-1-chloro-1-octene remaining. Hence, the migratory insertion reaction of the foregoing alpha-chloroalkenylalanate to form the vinylalane, HexHC=C(Me)AlMe₂, did occur.

(B) (7E, 9Z)-8-methyl-7,9-hexadecadiene via vinyl group migration

From the warmed solution of Example 1(A) gas chromatography analysis revealed an increase in 1-octyne (19%) and (7E, 9Z)-8-methyl-7,9-hexadecadiene in 12% yield. The formation of the diene is a result of a redistribution reaction occurring between the nucleophilic vinylalanate, [HexHC=C(Cl)AlMe₃]⁻Na⁺, and the electrophilic vinylalane, HexHC=C(Me)AlMe₂. Thus, the divinylalanate

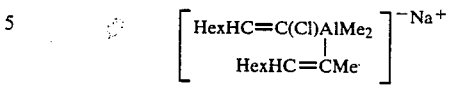

undergoes a vinyl group migration and eliminates sodium chloride to yield a dienylalane

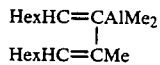

which affords (7E, 9Z)-8-methyl-7,9-hexadecadiene upon hydrolysis.

EXAMPLE 2

When it is desired to circumvent the redistribution reaction of Example 1(B), and thus the subsequent formation of the E, Z-conjugated dienyl species, the presence or generation of trigonal aluminum species must be avoided. Accordingly, addition of sodium methoxide (1.5 equivalent) to the reaction solution of Example 1(A) prior to the warming of the above vinylalanate, followed by heating at 50° C. for 18 hours, and protonolysis, afforded by GC analysis only cis-2-nonene (69%) and by-product 1-octyne (31%) upon hydrolysis. No trace of diene was detected. Moreover, the reaction is highly stereoselective since the ratio of cis:trans-2-nonene formed was >99.5:0.5.

EXAMPLES 3–6

Preparation of Ethylated Olefins

As shown in Table 1, the reaction of Example 2 also applies to sodium triethylaluminum hydride, furnishing the respective ethylated olefins.

TABLE 1

| R | R′ | Percent Yield of RHC=CR′Z, GC (isol.) | | Example |
|---|---|---|---|---|
| | | Z = H | Z = I | |
| n-$C_6H_{13}$ | $CH_3$ | 69 | (63) | 3 |
| n-$C_6H_{13}$ | $C_2H_5$ | 74 | (67) | 4 |
| n-$C_{10}H_{21}$ | $CH_3$ | 69 | — | 5 |
| n-$C_{10}H_{21}$ | $C_2H_5$ | 68 | — | 6 |

¹H-NMR examination showed that the triplet observed at 5.88 ppm for the above vinylalanate, [HexHC=C(Cl)AlMe₃]⁻Na⁺, disappeared after adding sodium methoxide and heating, with a new triplet of quartets (J=7, 2 Hz) present upfield at 5.37 ppm for the vinylic proton in the methoxyalanate, [HexHC=C(Me)AlMe₂(OMe)]Na⁺. By comparison, the alpha-chloroalkenylalanate, [HexHC=C(Cl)AlH₃]Li⁺ (prepared from treatment of 1-chloro-1-octyne with LiAlH₄ in diglyme according to the method of Zweifel, et al. J. Am. Chem. Soc., 1979, 101, 5101) exhibited a triplet of doublets (J=8, 3 Hz) at 5.98 ppm for the vinylic proton (see Miller, J. Org. Chem., Vol. 54, No. 5, 1989, refs. 12 and 13) while the methoxyvinyalanate, [BuHC=C(Bu)Al(i—Bu)₂(OMe)]⁻Na⁺ (derived from hydroalumination of 5-decyne with i-Bu₂AlH according to the method of Zweifel, et al., Organic Reactions, 1984, 32, 375 followed by treatment with NaOMe in diglyme) produced a triplet (J=7 Hz) at 5.44 ppm. The chemical shifts of the vinylic proton in the vinylalanates. [HexHC=C(Cl)AlMe$_3$]$^-$Na$^+$ and [HexHC=C(Me)AlMe$_2$(OMe)]$^-$Na$^+$, closely resembled those of known structure prepared by the methods of Zweifel, et al. This similarity supports the presence of the vinylalanates, [HexHC=C(Cl)Me$_3$]$^-$Na$^+$ and [HexHC=C(Me)AlMe$_2$(OMe)]$^-$Na$^+$, as intermediates in the reaction.

EXAMPLE 7

Preparation of trans-2-iodo-2-nonene

The vinyl C-Al bond can be functionalized in a variety of ways not possible for reactions involving the corresponding vinylborates. For example treatment of a diglyme solution of 1 equivalent of [HexHC=C(Me)AlMe$_2$(OMe)]$^{-Na+}$ with 1 equivalent of iodine ($-78°$ C. to room temperature) resulted in stereospecific iodination to afford the corresponding vinyl iodide (trans-2-iodo-2-nonene) in 63% yield. Thus, the entire sequence represents a useful synthesis of not only disubstituted olefins but stereodefined trisubstituted alkenes as well.

EXAMPLE 8

Preparation of cis-2-nonene and cis-3-tetradecene via intramolecular crossover migration (A) Unlike the corresponding alpha-chloroalkenylborates which spontaneously undergo migratory insertion even at low temperatures, the aloha-chloroalkenylalanates, [RHC=C(Cl)AlR'$_3$]$^-$Na$^+$, are stable at temperatures up to 0° C. As a result, it is possible to carry out crossover experiments to demonstrate the intramolecular nature of this rearrangement. Thus, to a mixture of sodium methoxide in diglyme were sequentially added at 0° C. HC=C(Cl)AlMe$_3$]$^-$Na$^+$ and [C$_{10}$H$_{21}$HC=C(Cl)AlEt$_3$]$^-$Na$^+$. The reaction mixture was heated at 50° C. for 18 hours and, following protonolysis, GC analysis showed the presence of only the alkenes, cis-C$_6$H$_{13}$CH=CHMe and cis-C$_{10}$H$_{21}$HC=CHEt which were derived from intramolecular transfer of carbon groups from Al to the adjacent vinylic carbon. None of the crossover products C$_6$H$_{13}$HC=CHEt and C$_{10}$H$_{21}$H=CHMe were detected.

(B) In a similar manner to Example 3A reaction of a mixture of [C$_6$H$_{13}$ HC=C(Cl)AlEt$_3$]$^-$Na$^+$ and [C$_{10}$H$_{21}$HC=C(Cl)AlMe$_3$]$^-$Na$^+$ produced only C$_6$H$_{13}$HC=CHEt and C$_{10}$H$_{21}$HC=CHMe.

The carbon group migration for Al to the adjacent vinylic center in the alpha-chloroalkenyl alanates is an intramolecular process.

EXAMPLE 9

Preparation of trans-2-Iodo-2-nonene

To a mixture of 0.24 g (8.0 mmol) of 80% sodium hydride and 8 mL of dry diglyme was added at 0° C. 3.75 mL (7.50 mmol) of 2.0M trimethylaluminum in hexane. The reaction mixture was warmed to room temperature, stirred for 2 hours, and then was filtered under argon through a medium glass frit. The hexane contained in the filtrate was removed under reduced pressure (25° C., 30 torr), and the clear solution of sodium trimethylaluminum hydride obtained was treated at 0° C. with 0.72 g (5.0 mmol) of 1-chloro-1-octyne and 0.70 mL (5.0 mmol) of n-heptane as an internal GC standard. The solution was stirred for one hour at 0° C. (hydrolysis of an aliquot at this point revealed by GC 89% trans-1-chloro-1-octene and 11% 1-octyne) and to the solution was added 0.40 g (7.5 mmol) of sodium methoxide. The mixture was then warmed to 50° C. and stirred overnight. Hydrolysis and GC analysis of an aliquot showed 69% cis-2-nonene (containing <0.5% trans-2-nonene) and 31% 1-octyne. The reaction was cooled to $-78°$ C. and treated with a solution of 1.59 g (6.25 mmol) of iodine in 5 mL of diglyme. After warming the reaction mixture to 25° C., GC examination of an aliquot showed complete iodination had occurred, as no residual cis-2-nonene was present after hydrolysis. However, due to the formation of some 1-iodo-1-octyne, the reaction solution was additionally treated with 1.0 mL (2.0 mmol) of 2.0M trimethylaluminum in hexane, which after 24 hours at room temperature had converted all 1-iodo-1-octyne into 1-octyne (after protonolysis), thereby simplifying the isolation procedure. The reaction mixture was slowly poured into a mixture of 3N HCl and pentane. The aqueous layer was extracted with pentane and the combined organic phase was washed sequentially with 3N HCl, saturated NaHCO$_3$, 20% Na$_2$SO$_3$, and saturated NaCl. Concentration and short-path distillation provided 0.79 g (63%) of the 2-iodo-2-nonene: bp=45./0.1 torr; IR (neat) 3020 (w), 2950 (s), 2920 (s), 2850 (s), 1638 (m), 1465 (m), 1455 (m), 1385 (m), 1135 (m), 1060 (m) cm$^{-1}$; $^1$H—NMR (CDCl$_3$, TMS) 0.90 (t, 3H), 1.2–1.5 (br s, 8H), 2.05 (m, 2H), 2.35 (d, J=1.5 Hz, 3H), 6.15 (tq, J=7.2, 1.5 Hz, 1H).

EXAMPLE 10

Preparation of trans-3-Iodo-3-Decene

To a mixture of 0.24 g (8.0 mmol) of 80% sodium hydride and 8 mL of dry diglyme was added at 0° C. 1.02 mL (7.50 mmol) of triethylaluminum. The reaction mixture was warmed to 50° C., stirred for 2 hours, and then was filtered under argon through a medium glass frit. The clear solution of sodium triethylaluminum hydride obtained was treated at 0° C. with 0.72 g (5.0 mmol) of 1-chloro-1-octyne and 0.90 mL (5.0 mmol) of n-nonane as an internal GC standard. The solution was stirred for one hour at 0° C. (hydrolysis of an aliquot at this point revealed by GC 89% trans-1-chloro-1-octene and 11% 1-octyne) and to the solution was added 0.40 g (7.5 mmol) of sodium methoxide. The mixture was then warmed to 50° C. and stirred overnight. Hydrolysis and GC analysis of an aliquot showed 74% cis-3-decene (containing, <0.5% trans-3-decene) and 26% 1-octyne. The reaction was cooled to $-78$.C and treated with a solution of 1.59 g (6.25 mmol) of iodine in 5 mL of diglyme. After warming the reaction mixture to 25° C., GC examination of an aliquot showed complete iodination had occurred, as no residual cis-3-decene was present after hydrolysis. However, due to the formation of some 1-iodo-1-octyne, the reaction solution was additionally treated with 0.28 mL (2.0 mmol) of triethylaluminum, which after 24 hours at room temperature had converted all 1-iodo-1-octyne into 1-octyne (after protonolysis), thereby simplifying the isolation procedure. The reaction mixture was slowly poured into a mixture of 3N HCl and pentane. The aqueous layer was extracted with pentane and the combined organic phase was washed sequentially with 3N HCl, sat. NaHCO$_3$, 20% Na$_2$SO$_3$, 20% Na$_2$SO$_3$, and sat. NaCl. Concentration and short-path distillation provided 0.89 g (67%) of the title compound: bp=55./0.2 torr; IR (neat) 3020 (w), 2960 (s), 2920 (s), 2860 (s), 1630 (m), 1460 (m), 1375 (m), 1255 (m), 1135 (m) cm$^{-1}$; $^1$H—NMR (CDCl$_3$, TMS) 0.85 (t, 3H$_{0, 0.95}$ (t, 3H), 1.2–5(br s, 8H), 2.05 (m, 2H), 2.40 (q, 2H), 6.15 (tt, J=7.5, 1 Hz, 1H).

EXAMPLE 11

Preparation of Cis-2-Tridecene

By a procedure similar to that described in Example 9, 1.00 g (5.00 mmol) of 1-chloro-1-dodecyne was hydroaluminated with sodium trimethylaluminum hydride and then treated with sodium methoxide. After heating the reaction mixture overnight at 50° C., it was slowly poured into a mixture of 3N HCl and pentane. The aqueous layer was extracted with pentane and the combined organic phase was washed sequentially with 3N HCl, saturated NaHCO$_3$, and saturated NaCl. Analysis by GC (using n-nonane as an internal standard) showed the presence of 2% 1-dodecene, 29% 1-dodecyne, and 69% cis-2-tridecene. Short-path distillation provided a pure sample of cis-2-tridecene; bp=49./0.2 torr; IR (neat) 3050 (w), 2960 (m), 2920 (s), 2850 (s), 1660 (w), 1470 (m) cm$^{-1}$; $^1H$—NMR (CDCl$_3$, TMS) (ppm) 0.85 (t, 3H), 1.2 -1.4 (br s, 16H), 1.55 (d, J=6 Hz, 3H), 2.0 (m, 2H), 5.40 (m, 2H).

EXAMPLE 12

Preparation of Cis-3-Tetradecene

In a manner similar to that described in Example 10, 1.00 g (5.00 mmol) of 1-Chloro-1-dodecyne was hydroaluminated with sodium triethylaluminum hydride and then treated with sodium methoxide. After heating the reaction mixture overnight at 50° C., it was slowly poured into a mixture of 3N HCl and pentane. The aqueous layer was extracted with pentane and the combined organic phase was washed sequentially with 3N HCl, saturated NaHCO$_3$, and saturated NaCl. Analysis by GC (using n-nonane as an internal standard) showed the presence of 4% 1-dodecene, 28% 1-dodecyne, and 68% cis-3-tetradecene. Short-path distillation provided a pure sample of cis-3-tetradecene: bp=57./0.1 torr; IR (neat) 3020 (w), 2960 (s), 2920 (s), 2850 (s), 1655 (w), 1470 (m) cm$^{-1}$; $^1H$—NMR (CDC$_{13}$, TMS) 0.85 (t, 3H), 0.95 (t, 3H), 1.2–1.4 (br s, 16H), 2.05 (m, 4H), 5.35 (m, 2H).

EXAMPLE 13

Crossover Experiments

A slurry of 0.31 q (6.0 mmol) of sodium methoxide in diglyme was treated sequentially at 0° C. with cold (0° C.) solutions of the alpha-chloroalkenylalanates (2.0 mmol each) derived from 1-chloro-1-octyne/sodium trimethylaluminum hydride and 1-chloro-1-dodecyne/sodium triethylaluminum hydride (both prepared analogously to that described above). The reaction mixture was heated at 50° C. overnight and an aliquot was withdrawn and hydrolyzed. GC analysis showed the presence of cis-2-nonene (60%) and cis-3-tetradecene (65%) with none of either of the crossover products cis-3-decene or cis-2-tridecene detected.

A similar crossover experiment using the alpha-chloroalkenylalanates derived from 1-chloro-1-octyne/sodium triethylaluminum hydride and 1-chloro-1-dodecyne/sodium trimethylaluminum hydride produced (by GC examination of a hydrolyzed aliquot) only the intramolecular transfer products cis-3-decene (72%) and cis-2-tridecene (66%). Neither of the crossover adducts cis-3-tetradecene and cis-2-nonene was detected.

The above disclosure has been presented for purposes of illustration and not limitation. As can readily be appreciated by those skilled in the art, this invention is susceptible to considerable variation in its practice within the spirit and scope of the ensuing claims.

What is claimed is:

1. A process for production of a compound of the formula [RHC=CR'AlR'$_2$(OR")]$^-$M$^+$ in which the alkenyl group is predominantly (E) in structure, which comprises reacting a compound of the formula MOR" with a compound of the formula [RHC=C(X)AlR'$_3$]$^-$M$^+$ in which the alkenyl group is predominantly (E) in structure in a non-protonic polar solvent
   wherein R, R' and R" are the same or different and each is an inert carbon-bonded organic group; X is a halogen atom; and M is an alkali metal atom; such that one R' group undergoes 1,2-migration to the carbon atom of the alkenyl group.

2. A process of claim 1 wherein MOR" is a sodium alkoxide or a potassium alkoxide and wherein the alkali metal of [RHC=C(X)AlR'$^3$]$^-$M$^+$ is sodium, potassium, or lithium.

3. A process of claim 1 wherein X is a chlorine or bromine atom.

4. A process of claim 1 wherein MOR" is a sodium alkoxide or a potassium alkoxide; wherein the alkali metal of [RHC=C(X)AlR'$^3$]$^-$M$^+$ is sodium, potassium, or lithium; and wherein X is a chlorine or bromine atom.

5. A process of claim 1 for production of an alkali metal alkenyl(alkoxy)dialkylalanate in which the alkenyl group is predominantly (E) in structure, which comprises reacting an alkali metal alkoxide with an alkali metal(trans-1-halo-1-alkenyl)trialkylalanate in a non-protonic polar solvent, such that an alkyl group attached to the aluminum atom undergoes 1,2-migration to the carbon atom of the alkenyl group which is attached to the aluminum atom.

6. A process of claim 5 wherein the alkali metal alkoxide is a sodium alkoxide, and wherein the alkali metal (E-1-halo-1-alkenyl)trialkylalanate is a sodium (E-1-halo1-alkenyl)trialkylalanate.

7. A process of claim 5 wherein the halogen atom of the alkali metal (E-1-halo-1-alkenyl)trialkylalanate is a chlorine or bromine atom.

8. A process of claim 5 wherein the alkali metal alkoxide is a sodium alkoxide, and wherein the alkali metal (E-1-chloro-1-alkenyl)trialkylanate is a sodium (E-1-chloro1-alkenyl)trialkylalanate.

9. A process for production of a compound of the formula RHC=CR'AlR'$_2$ in which the alkenyl group is predominantly E in structure, which comprises warming a cold solution of a compound of the formula [RHC=C(X)AlR'$_3$]$^-$M$^+$ in which the alkenyl group is predominantly E in structure in a non-protonic polar solvent wherein R and R' can be the same or different and each is an inert carbon-bonded organic group; X is a halogen atom; and M is a alkali metal atom; such that one of the R' groups attached to the aluminum atom undergoes 1,2-migration to the carbon atom of the alkenyl group which is attached to the aluminum atom.

10. A process of claim 9 wherein M is sodium, potassium, or lithium.

11. A process of claim 9 wherein X is a chlorine or bromine atom.

12. A process of claim 9 wherein M is a sodium, potassium, or lithium cation and wherein X is a chlorine or bromine atom.

13. A process of claim 9 for production of an dialkylalkenylalane in which the alkenyl group is predominantly E in structure, which comprises warming a cold solution of an alkali metal (E-1-halo-1-alkenyl)trialkylalanate in a non-protonic polar solvent, such that an alkyl group attached to the aluminum atom undergoes 1,2-migration to the carbon atom of the alkenyl group which is attached to the aluminum atom.

14. A process of claim 13 wherein the alkali metal (E-1-halo-1-alkenyl)trialkylalanate is a sodium (E-1-halo-1alkenyl)trialkylalanate.

15. A process of claim 13 wherein the halogen atom of the alkali metal (E-1-halo-1-alkenyl)trialkylalanate is a chlorine or bromine atom.

16. A process of claim 13 wherein the alkali metal (E-1-halo-1-alkenyl)trialkylalanate is a sodium (E-1-chloro-1alkenyl)trialkylalanate.

17. A process for production of a compound of the formula

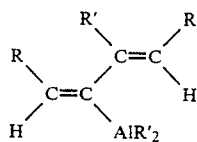

in which the conjugated olefinic groups are predominantly E in structure (or carbon groups of each olefinic group are predominantly cis to one another), which comprises warming a cold solution of a compound of the formula $[RHC{=}C(X)AlR'_3]^-M^+$, in which the alkenyl group is predominantly E in structure, in a non-protonic polar solvent, to cause the formation of an intermediate of the formula $RHC{=}C(R')AlR'_2$ to result in reactions in accordance with the equation

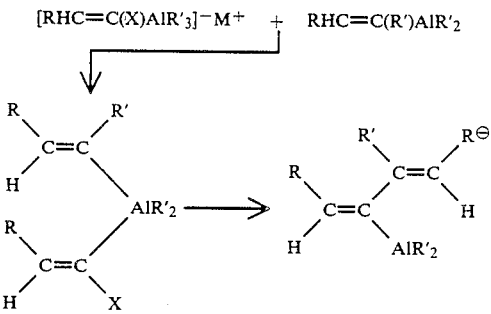

wherein R and R' can be the same or different and each is an inert carbon-bonded organic group; X is a halogen atom; and M is a alkali metal atom; such that an R' group attached to the aluminum atom undergoes 1,2-migration to the carbon atom of the alkenyl group which is attached to the aluminum atom.

18. A process of claim 17 wherein M is sodium, potassium, or lithium.

19. A process of claim 17 wherein X is a chlorine or bromine atom.

20. A process of claim 17 wherein M is a sodium, potassium, or lithium cation and wherein X is a chlorine or bromine atom.

21. A process of claim 17 for production of an alkali metal (E,E)-3-alkyl-2-dialkylalumino-1,3-diene, which comprises warming a cold solution of an alkali metal (E-1-halo-1-alkenyl)trialkylalanate in a non-protonic polar solvent, such that an intermediate E-1-alkyl-1-alkenyl(dialkyl)alane redistributes with the alkali metal (E-1-halo-1-alkenyl)trialkylalanate to form an alkali metal E-1-alkyl-1-alkenyl(E-1-halo-1-alkenyl)dialkylalanate, and, in the latter, the cis-1-alkyl-1-alkenyl group undergoes 1,2-migration to the carbon atom of the trans-1-halo-1-alkenyl group attached to the aluminum atom.

22. A process of claim 18 wherein the alkali metal (E-1-halo-1-alkenyl)trialkylalanate is a sodium (E-1-halo-1-alkenyl)trialkylalanate.

23. A process of claim 18 wherein the halogen atom of the alkali metal (E-1-halo-1-alkenyl)trialkylalanate is a chlorine or bromine atom.

24. A process of claim 18 wherein the alkali metal (E-1-halo-1-alkenyl)trialkylalanate is a sodium (E-1-chloro-1-alkenyl)trialkylalanate.

25. An alkali metal alanate of the formula $[RHC{=}C(R')AlR'_2(OR'')]^-M^+$ in which the alkenyl group is predominantly E in structure and wherein R, R' and R'' can be the same or different and each is an inert carbon-bonded organic group; X is a halogen atom; and M is an alkali metal atom.

26. A compound of claim 25 wherein X is a chlorine or bromine atom and M is sodium, potassium, or lithium.

27. A compound of claim 25 wherein R, R' and R'' are hydrocarbyl groups consisting solely of carbon and hydrogen.

28. An alkali metal compound of the formula

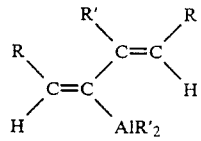

in which the alkenyl group is predominantly E in structure and wherein R and R' can be the same or different and each is an inert carbon-bonded organic group; X is a halogen atom; and M is an alkali metal atom.

29. A compound of claim 28 wherein X is a chlorine or bromine atom and M is sodium, potassium, or lithium.

30. A compound of claim 28 wherein R, R' and R'' are hydrocarbyl groups consisting solely of carbon and hydrogen.

31. A trisubstituted conjugated alkadiene of the formula

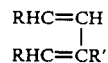

wherein R and R' are hydrocarbyl groups consisting solely of carbon and hydrogen and the conjugated olefinic groups are predominantly cis in structure with respect to the carbon groups on each separate olefinic unit.

* * * * *